United States Patent [19]
Brinkerhoff et al.

[11] Patent Number: 5,354,312
[45] Date of Patent: Oct. 11, 1994

[54] ENDOSCOPIC ANVIL GRASPING INSTRUMENT

[75] Inventors: Ronald J. Brinkerhoff, New Richmond; Edward J. Biehle, IV, Westchester; Richard W. Flaker, Fairfield; Julia C. Putnam, Cincinnati, all of Ohio

[73] Assignee: Ethicon, Inc., Somerville, N.J.

[21] Appl. No.: 947,197

[22] Filed: Sep. 18, 1992

[51] Int. Cl.$^5$ ............................................. A61B 17/00
[52] U.S. Cl. ...................................... 606/207; 606/205
[58] Field of Search ........ 606/151, 152, 153, 205–209, 606/139, 142; 128/751, 755

[56] References Cited

U.S. PATENT DOCUMENTS

| | | | |
|---|---|---|---|
| 2,507,710 | 5/1950 | Grosso | 606/208 |
| 3,258,012 | 6/1966 | Nakayama et al. | 606/153 |
| 3,828,791 | 8/1974 | Santos | 606/207 |
| 4,038,987 | 8/1977 | Komiya . | |
| 4,427,014 | 1/1984 | Bel et al. | 606/206 |
| 4,553,543 | 11/1985 | Amarasinghe | 606/153 |
| 4,873,975 | 10/1989 | Walsh et al. | 606/153 |
| 5,170,800 | 12/1992 | Smith et al. | 606/205 |
| 5,171,258 | 12/1992 | Bales et al. | 606/205 |
| 5,176,699 | 1/1993 | Markham | 606/207 |
| 5,209,747 | 5/1993 | Knoepfler | 606/205 |

FOREIGN PATENT DOCUMENTS

| | | | |
|---|---|---|---|
| 4027570 | 3/1992 | Fed. Rep. of Germany . | |
| 646858 | 12/1984 | Switzerland | 606/207 |
| 219095 | 5/1968 | U.S.S.R. | 606/207 |

OTHER PUBLICATIONS

Verbrugge, *Journal of Bone & Joint Surgery* vol. 35-A, No. 3, Jul. 1953 p. 773.

*Primary Examiner*—Ralph Lewis
*Attorney, Agent, or Firm*—Paul A. Coletti

[57] ABSTRACT

An endoscopic surgical instrument is disclosed which is particularly facilitated for grasping the anvil portion of an circular surgical stapling device. The present instrument includes a generally elongated shaft, with a pair of cooperating jaw members disposed at the distal end of the shaft. The jaw members cooperate in a pincer-like action for gripping the anvil portion of the associated surgical stapler therebetween. The jaw members include cooperating jaw portions, each of which defines a semi-cylindrical gripping surface. The jaw portions are angularly disposed relative to the longitudinal axis of the associated shaft, and are otherwise configured to facilitate gripping and manipulation of the anvil portion of the surgical stapling device, as well as tissue manipulation.

9 Claims, 3 Drawing Sheets

5,354,312

ENDOSCOPIC ANVIL GRASPING INSTRUMENT

FIELD OF THE INVENTION

This invention relates generally to an endoscopic surgical instrument. More particularly, the invention relates to an endoscopic surgical instrument extendable through a trocar cannula for grasping and holding the shaft of the anvil portion of an internal circular surgical stapling device to facilitate insertion and manipulation of the anvil portion.

BACKGROUND OF THE INVENTION

Generally, surgical stapling has made substantial advances in the past decades. Specifically, in the area of internal anastomotic stapling the advances have been quite dramatic. Devices such as the Proximate ™ ILS stapler, produced by the assignee of the present invention, Ethicon, Inc., Somerville, N.J., have enabled surgeons to perform operations and procedures which were heretofore perceived as difficult, if not impossible, with relative ease. One example of such a device is disclosed in U.S. Pat. No. 5,104,025.

In performing surgical anastomotic stapling, generally the two pieces of lumen are attached by a ring of staples. During this procedure, a circular knife blade is used to separate tissue which is held within the circular ring. The circular ring is then removed with the stapler so that a circular opening within the lumen is completed along the surgical stapling line.

In performing these surgical procedures it is often necessary to separate the anvil portion on which the staples are clinched from the stapling portion from which the staples are expelled. The end of one of the lumens is attached to the shaft of the anvil portion for example by a purse string suture, and the end of the other lumen is attached to the stapling portion such as by another purse string suture, or other technique. It is then necessary to grasp and hold the anvil shaft to reattach the anvil portion to the stapling portion.

It has heretofore been the practice to use instruments not particularly suited or configured to grasp and hold the anvil shaft, such as conventional forceps that include jaw portions to grasp the anvil shaft. It has recently been proposed to utilize special forceps that include jaw portions that are configured to grasp and hold the anvil shaft. The jaw portions include semi-cylindrical grasping surfaces to contact the outer surface of the anvil shaft. The grasping surfaces are smooth to maximize the surface area in contact with the anvil shaft. The heretofore used forceps are not intended to be inserted into an anatomical cavity through a trocar cannula.

There is a need for a surgical instrument for grasping and holding an anvil shaft of an internal, circular surgical stapling device that is extendable through a trocar cannula. It is necessary that such a device securely grasp the anvil shaft and be able to manipulate the anvil portion when extended deep into the pelvis area or other surgical region.

SUMMARY OF THE INVENTION

An endoscopic surgical instrument is provided to grasp and hold the shaft of the anvil portion of an internal, circular surgical stapling device. The anvil grasping surgical instrument is extendable into an anatomical cavity through a trocar cannula. The present instrument can be configured for single-patient disposable use, or for multiple uses.

The surgical instrument includes an elongated shaft having an outer diameter that is less than the inner diameter of the trocar cannula. A pair of jaw members are disposed at the distal end of the shaft. The jaw members include semi-cylindrical distal jaw portions for grasping a rod-like anvil shaft therebetween. The proximal portions of the jaw members are pivotally mounted adjacent to the distal end of the shaft to permit movement of the jaw members between a first or closed position wherein the jaw portions are positioned adjacent one another in grasping relationship to an anvil shaft positioned therebetween and a second or open position wherein the jaw portions are separated to permit an anvil shaft to pass therebetween. The jaw portions when in their first position have an outer dimension that is no greater than the outer diameter of the instrument shaft to thereby allow passage.

An actuation means extends through the shaft for moving the jaw portions between their first and second positions. A handle is disposed at the proximal end of the shaft that includes a means connected to the actuation means for controlling the movement of the jaw portions.

The jaw portions are oriented such that a plane passing through the jaw portions intersects the longitudinal axis of the shaft at an acute angle in the range from about 40 degrees to about 60 degrees and preferably about 50 degrees. The proximal portions of the jaw members when in their first position extend outwardly from the distal end of the shaft a distance such that there is clearance between the anvil and the shaft when the jaw portions grasp the anvil shaft in an orientation wherein the axis of the anvil shaft forms an acute included angle with the shaft.

DESCRIPTION OF THE DRAWING

A more complete appreciation of this invention and many of the attendant advantages thereof will be readily apparent as the same becomes better understood by reference to the following detailed description, when considered in conjunction with the accompanying drawings, in which like reference numerals indicate the same or similar components, wherein.

DETAILED DESCRIPTION OF THE DRAWING

Figure 1:
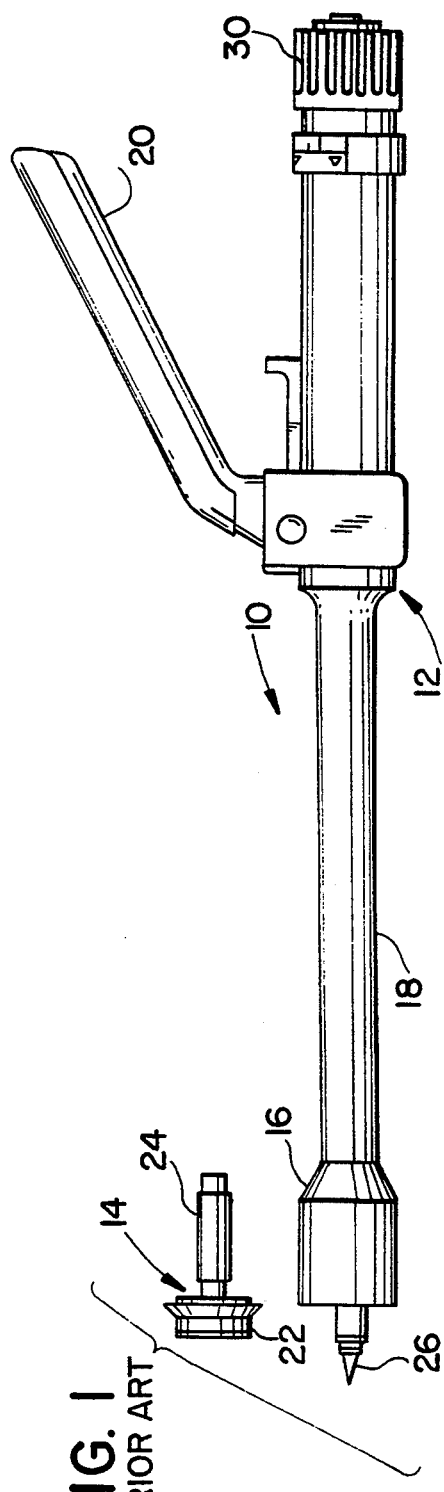
FIG. 1 is a side elevational view of an exemplary internal circular surgical stapling device that includes a separable anvil portion.

Referring to FIG. 1, there is shown an exemplary internal circular surgical stapling device 10 of the type disclosed in U.S. Pat. No. 5,104,025, which patent is owned by the same assignee of the present invention and the disclosure of which is incorporated herein by reference.

Stapler 10 includes a stapler portion 12 and an anvil portion 14. Stapler portion 12 includes a stapler head 16 from which staples are expelled, a shaft 18 which contains a firing mechanism, and a trigger 20 which activates the firing mechanism. Anvil portion 14 includes an anvil head 22 and an anvil shaft 24. Anvil head 22 includes circumferentially displaced anvil pockets (not shown) that are aligned to receive and clinch the staples expelled from the stapler head upon activation of trigger 20. A knife blade (not shown) is held within the stapler head 16 to cut out tissue held or located within the circumference of the stapled tissue. In so doing, the anvil can be extracted or removed through the opening that has been cut, and the stapler extracted from the anastomotic site.

Stapler head 16 is provided with a trocar shaft 26 that is capable of piercing tissue. During use, purse-stringed tissue is typically positioned to surround shaft 26, with the shaft projecting therefrom. Similarly, anvil shaft 24 may be placed within a lumen of tissue and the tissue purse-stringed about shaft 24. Prior to firing of the stapling device it is necessary to orient the anvil portion 14 relative to the stapler portion 12 so that the anvil shaft 24 is placed over and attached to the trocar shaft 26. Rotation of the adjustment screw 30 is effective to cause the anvil portion 24 to move toward the stapler portion 12.

The present invention is directed to a surgical instrument that is specifically intended for use in grasping and holding the anvil shaft 24 during insertion and securing of the anvil portion, and then for attaching the anvil portion to the stapling portion. The present instrument is also particularly suited for detaching the anvil portion from the stapling device, as well as for other manipulation of the anvil portion. The present instrument is further preferably configured to facilitate tissue manipulation, thus enhancing versatile use of the instrument.

Figure 2:
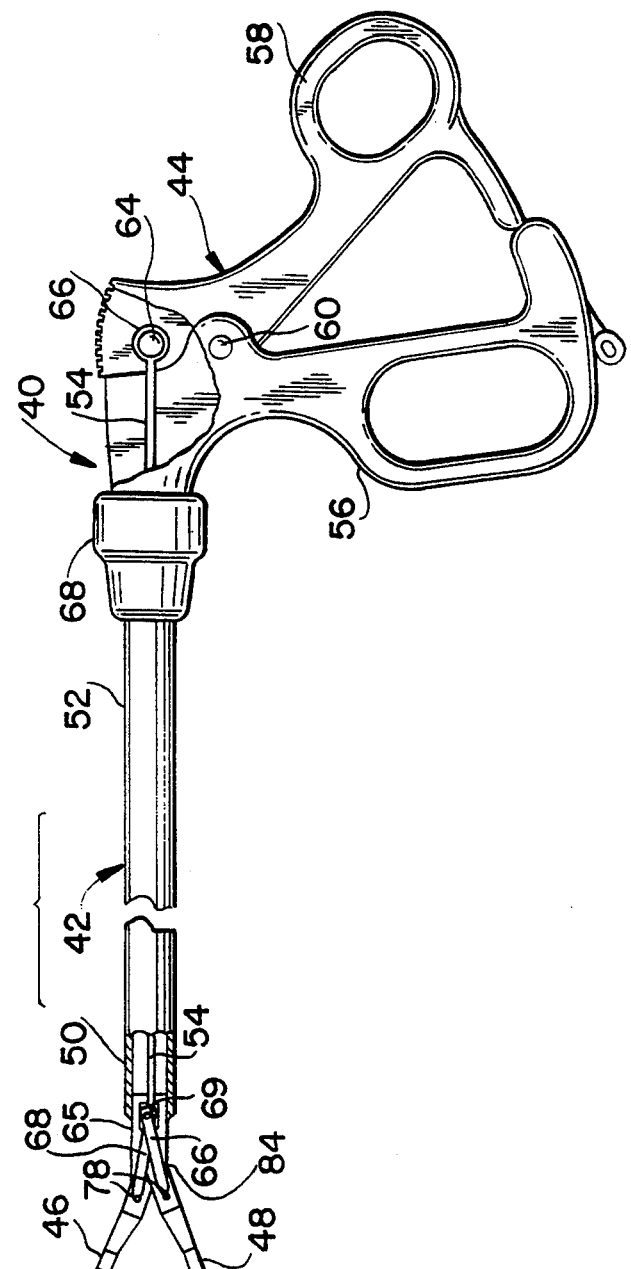
FIG. 2 is a side elevational view, partially broken away, of an endoscopic surgical instrument constructed in accordance with the invention with the jaws in their open position.
Figure 3:
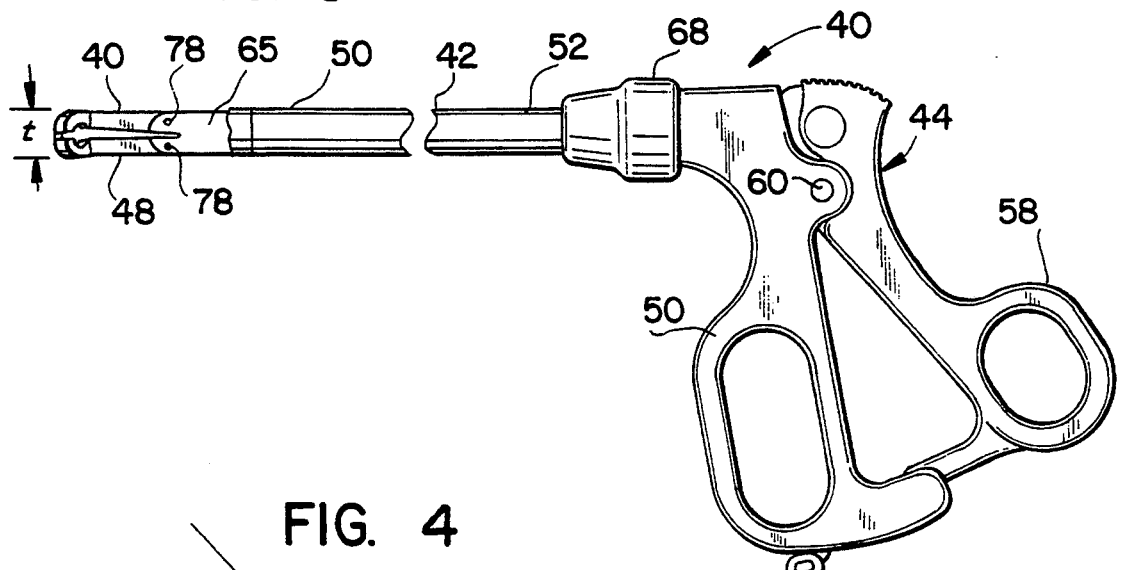
FIG. 3 is a side elevational view of the instrument shown in FIG. 2 with the jaws in their closed position.

Referring to FIGS. 2 and 3, there is shown an endoscopic surgical instrument 40 constructed in accordance with a preferred embodiment of the invention. Surgical instrument 40 includes an elongated shaft 42, a handle 44, and a pair of jaw members 46, 48. Elongated shaft 42 includes a distal end portion 50 and a proximal end portion 52. The outer diameter of shaft 42 is preferably about 10 mm so that it is extendable through a 10 mm trocar cannula. The jaw members 46, 48 are disposed at the distal end of the shaft 42 in a manner that will hereinbelow be described in further detail. The handle 44 is disposed at the proximal end of the shaft 42. A reciprocable actuation means, in the form of a push rod 54, extends through the shaft 42 for actuating the movement of the jaw members 46, 48.

The construction and operation of actuation means, including push rod 54, and handle 44 are similar to that shown and disclosed in U.S. Pat. No. 5,133,736, the disclosure of which patent is incorporated herein by reference. Handle 44 includes a fixed handle portion 56 and pivot handle portion 58 pivotally connected at pivot pin 60. The proximal end of push rod 54 is attached to a pivot member 64 that is received in a chamber 66 formed in handle portion 58. Upon pivotal motion of handle portion 58, using a conventional hand grip to apply pressure to handle portion 58, push rod 54 moves reciprocably and linearly within shaft 42. A control knob 68 is attached to shaft 42 to facilitate the rotation of the shaft and the jaw members 46, 48 attached thereto. Rotation of shaft 42 causes the rotation of rod 54 about pivot member 64. Knob 68 may be provided with means to retain the shaft and the jaw members in a selected orientation with respect to the handle, as is well known in the art.

The distal end of the push rod 54 extends into a clevis member 65 that is fixedly engaged by and extends distally from shaft 42. The jaw members 46, 48 are pivotally attached at the distal end of clevis member 65. The configuration of the jaw members are discussed in detail below. Each of the jaw members has a proximal portion that is pivotally engaged by the distal end of a corresponding connecting or linkage member 66, 68. The proximal end of the linkage members 66, 68 are pivotally connected to a flattened plate-like distal portion 69 of push rod 54. Movement of push rod 54 causes the jaw members 46, 48 to move between their first and second positions as discussed below.

Figure 6:
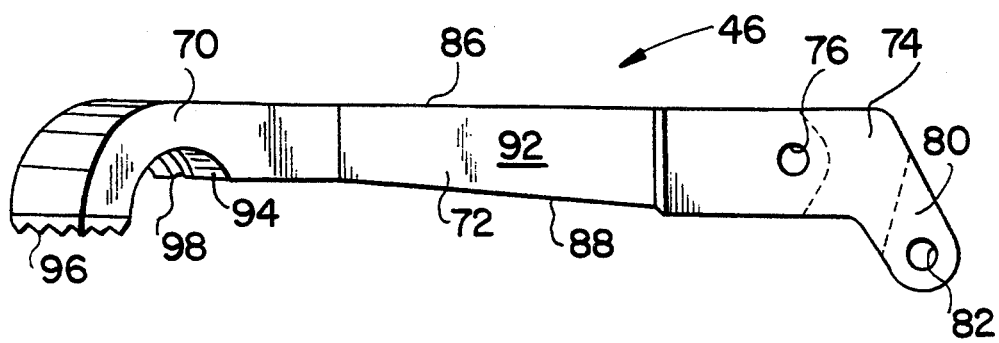
FIG. 6 is a top plan view of one of the jaw members of the present instrument constructed in accordance with a preferred embodiment of the invention.
Figure 7:
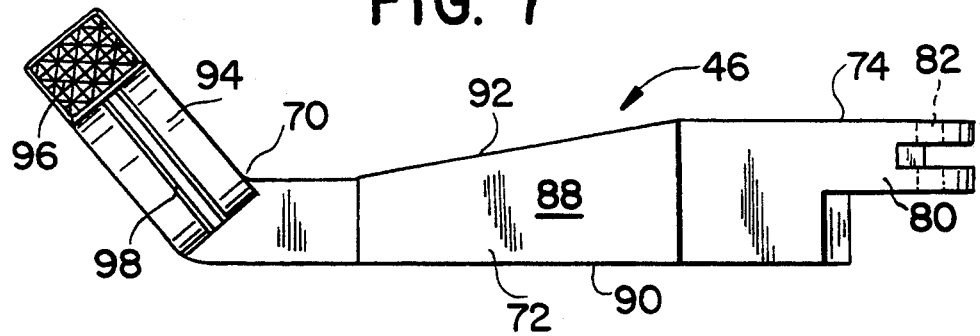
FIG. 7 is a side elevational view of the jaw member shown in FIG. 6.

The present invention is specifically directed to the unique configuration of the jaw members 46, 48. Referring to FIGS. 6 and 7, there is shown a jaw member 46. Jaw member 48 is the mirror image of jaw member 46, except that the proximal portion thereof is configured to permit pivotal connection to the jaw member 46. Jaw member 46 includes a distal jaw portion 70, an elongated central portion 72, and a proximal connecting portion 74.

Figure 4:
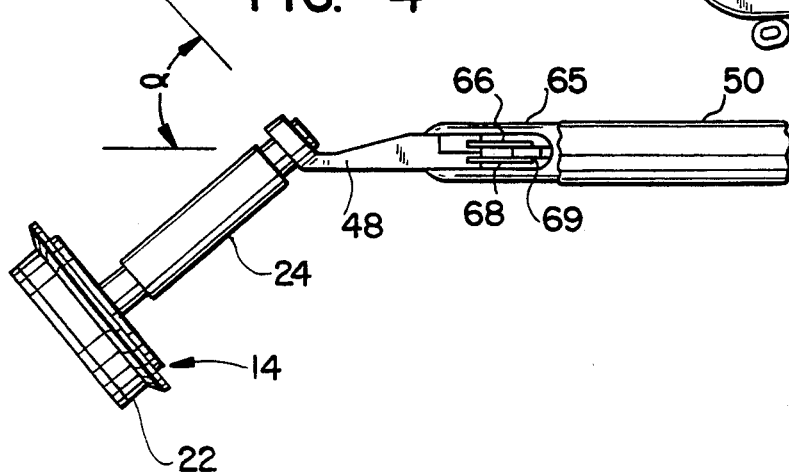
FIG. 4 is a side elevational view of the distal end portion of the surgical instrument grasping the shaft of an anvil portion in an orientation to permit the insertion thereof through a large diameter trocar cannula.
Figure 5:
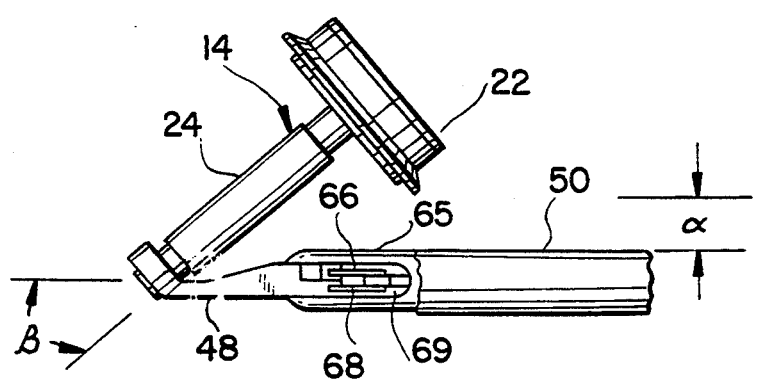
FIG. 5 is a side elevational view of the distal end portion of the surgical instrument grasping the shaft of an anvil portion in an orientation to facilitate the detachment and attachment of the anvil portion to the stapling portion.

Connecting portion 74 has an opening 76 formed therein through which a pivot pin 78 extends to pivotally connect jaw member 46 to clevis member 65, as shown in FIGS. 2 and 3. The proximal end of connecting portion 74 is formed with a proximally extending yoke 80 having an opening 82 formed therethrough. The respective one of linkage members 66, 68 extends into yoke 80 and is pivotally connected thereto by a pivot pin 84 (FIG. 2). The yokes 80 of jaw members 46, 48 are offset with respect to one another so that one is offset and positioned below the other, as best seen in FIGS. 4 and 5.

The central portions 72 of the jaw members 46, 48 is configured to extend axially with respect to the distal end of shaft 42 when the jaw members are in their first or closed position. The outer side surfaces 86 of the central portions of the jaw members 46, 48 are smooth and atraumatic, and are preferably spaced apart a distance no greater than the outer diameter of shaft 42 when the jaw members are in their first or closed position. The inner side surfaces 88 of the central portions of the jaw members preferably diverge as they extend distally when the jaw members are in their first or closed position. The bottom surfaces 90 of the central portions of the jaw members are generally flat, and horizontally disposed. In contrast, the upper surfaces 92 are generally flat, and inclined to extend distally toward the bottom surfaces 90.

The jaw portions 70 of the jaw members 46, 48 are preferably configured to define semi-cylindrical surfaces 94 for grasping the shaft 24 of the anvil portion 14. However, it will be appreciated that similarly shaped, non-smooth gripping surfaces, can alternately be employed, such as semi-octagonal surfaces.

The configuration of jaw members 46, 48 particularly facilitates versatile use of the present instrument. As best shown in FIG. 3, jaw members 46, 48 are configured and dimensioned such that when in their first, closed position, the distance between the outside surfaces of the jaw members (i.e., the outer dimension thereof, designated "t" in FIG. 3) is no greater than the outside diameter of the shaft 42 of the instrument. As such, insertion of the device down a trocar cannula dimensioned for the desired fit with the shaft 42 is permitted.

The angularity of the jaw portions 70 of the jaw members 46, 48, relative to the longitudinal axis of the instrument shaft, further facilitates the desired gripping action with the associated stapler anvil 14. As shown in FIG. 4, the jaw portions of the jaw members 46, 48 are oriented such that a plane passing through the jaw portions intersects the longitudinal axis of shaft 42 at an acute angle "alpha" in the range from about 40° to about 60°, and preferably about 50°. This configuration primarily facilitates grasping of the anvil for insertion through a relatively large trocar cannula.

The angularity of the jaw portions further facilitates gripping of anvil portion 14 in the orientation illustrated in FIG. 5. As will be noted, the proximal portions of the jaw members, when the jaw members are in their first closed position, extend outwardly from the distal end of the elongated shaft a distance such that there is clearance (designated "c" in FIG. 5), between the anvil and the elongated shaft when the jaw portions grasp the anvil shaft in the illustrated orientation. In this orientation, the axis of the anvil shaft forms an acute included angle "beta", preferably between about 30 degrees and about 50 degrees, and most preferably about 40 degrees, with the elongated shaft. This relative dimensioning primarily facilitates grasping of the anvil shaft 24 for manipulation of the anvil relative to the surgical stapling device 10.

As noted, the jaw portion of each of the jaw members 46, 48 is configured to define a semi-cylindrical gripping surface at 94. Additionally, the distal end portion of each of the jaw portions preferably comprises a textured gripping surface 96 to facilitate tissue manipulation. It is further preferred that the jaw portions of the jaw members be configured to define a clearance between the distal end portions thereof when the jaw portions are positioned in the first position, in grasping relationship with the anvil shaft, to thereby maximize gripping engagement with the anvil shaft. As will be appreciated, the provision of such a clearance between the distal end portions of the jaw members permits the jaw members to fully engage the associated anvil shaft with full gripping force.

In the embodiment of the jaw members illustrated in FIGS. 6 and 7, means are provided for enhancing gripping pressure of the jaw members with the associated anvil shaft. In this embodiment, gripping pressure is enhanced by the provision of at least one elongated gripping land 98 which extends along the length of the respective jaw portion, i.e., circumferentially of the semi-cylindrical gripping surface. As will be appreciated, the provision of this gripping land 98 acts to localize and concentrate gripping pressure exerted by the jaw members 46, 48, by effectively reducing the surface area through which gripping force is applied, thereby facilitating secure and firm grasping of the anvil shaft. As will be appreciated, the arrangement of the jaw portions mechanically enhances gripping engagement with the anvil shaft, in distinction from the provision of a rubberized gripping surface or the like intended to provide an increased coefficient of friction for the jaw portions.

Figure 8:
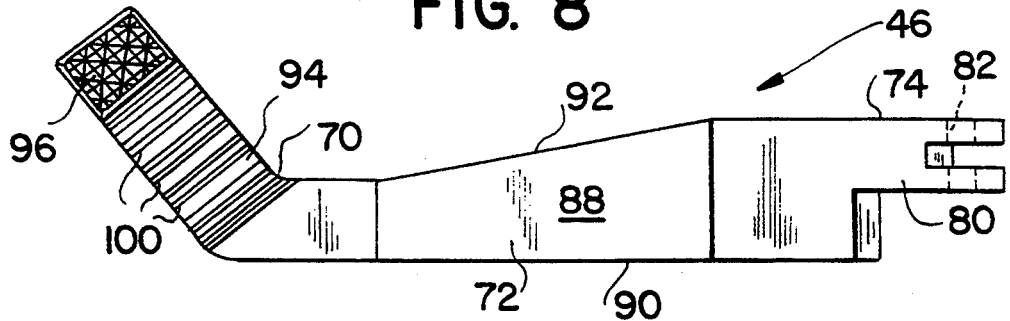
FIG. 8 is a side elevational view of a jaw member constructed in accordance with an alternative preferred embodiment of the invention.

FIG. 8 illustrates an alternate embodiment of the jaw members 46, 48, wherein the gripping enhancement for the jaw portions of the jaw members is provided by a plurality of gripping teeth 100 which extend transversely of each jaw portion across the width or lesser dimension thereof (i.e., in alignment with the axis which defines the semi-cylindrical gripping surfaces 94). Teeth 100 may be configured in a spline-like form, or more flat-crested. Again, these gripping teeth act to concentrate and localize gripping pressure, thereby facilitating secure grasping of anvil shaft 24.

Figure 9:
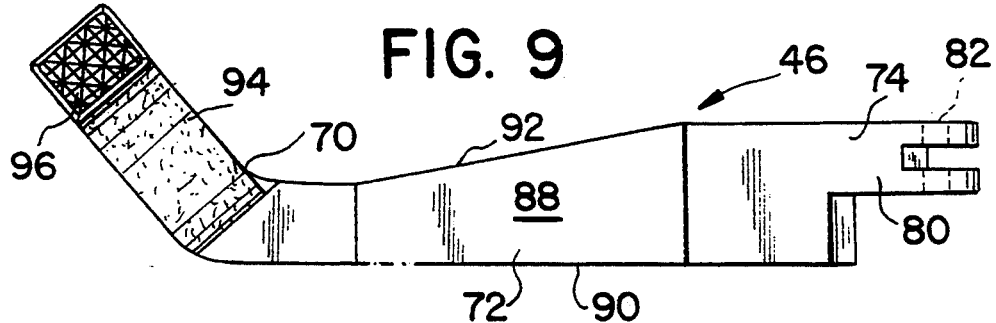
FIG. 9 is a side elevational view of a jaw member constructed in accordance with another alternative preferred embodiment of the invention.

FIG. 9 illustrates a further alternate embodiment, wherein gripping engagement with the associated anvil shaft is enhanced by the provision of a textured gripping surface at 94 along the semi-cylindrical gripping surface of each jaw portion.

From the foregoing, it will be observed that numerous modifications and variations can be effected without departing from the true spirit and scope of the novel concept of the present invention. It will be understood that no limitation with respect to the specific embodiments is intended or should be inferred. The disclosure is intended to cover all such embodiments as fall within the scope of the appended claims.

What is claimed is:

1. An endoscopic surgical instrument that is extendable into an anatomical cavity through a trocar cannula having an inner diameter for grasping a shaft of the anvil portion of a circular surgical stapling device, said anvil grasping surgical instrument comprising:

an elongated shaft describing a longitudinal axis and having an outer diameter that is less than the inner diameter of the trocar cannula so as to permit said elongated shaft to extend through the trocar cannula, said elongated shaft having a distal end and a proximal end;

a pair of jaw members having a length and defining a width therealong, said jaw members disposed at and extending from the distal end of said elongated shaft, said jaw members similarly defining a jaw axis extending in a distal direction along said jaw member length from the distal end of said elongated shaft and said jaw members including distal jaw portions defining semi-cylindrical surfaces formed along the entire width of said jaw members for grasping a rod-like anvil shaft therebetween, said jaw members including proximal portions that are pivotally mounted adjacent to the distal end of said elongated shaft so as to permit movement of said jaw portions between: (i) a first position wherein said jaw portions are positioned adjacent one another in grasping relation to an anvil shaft positioned on said semi-cylindrical surfaces; and (ii) a second position wherein said jaw portions are separated to permit an anvil shaft to pass therebetween, said jaw portions when in their first position having an outer dimension that is no greater than the outer diameter of said elongated shaft; and wherein said jaw portions are oriented such that said jaw axis intersects the longitudinal axis of said elongated shaft at an acute angle in the range from about 40 degrees to about 60 degrees; and actuation means extending through said elongated shaft having a proximal end portion and a distal end portion that is connected to said proximal portions of said jaw members for moving said jaw portions between their first and second positions.

2. The invention as defined in claim 1 wherein said acute angle is about 50 degrees.

3. The invention as defined in claim 1 wherein said proximal portions of said jaw members when said jaw members are in their first position extend outwardly from the distal end of said elongated shaft a distance such that there is clearance between the anvil and said elongated shaft when said jaw portions grasp the anvil shaft in an orientation wherein the axis of the anvil shaft forms an acute included angle with said elongated shaft.

4. The invention as defined in claims 1, wherein each said jaw portion includes gripping means for enhancing gripping pressure with the anvil shaft of the stapling device.

5. The invention as defined in claim 4, wherein said gripping means comprises at least one elongated gripping surface extending along the length of the jaw portion.

6. The invention as defined in claim 4, wherein said gripping means comprise a plurality of gripping teeth extending across the width of the jaw portion.

7. The invention as defined in claim 4, wherein said gripping means comprises a textured surface.

8. The invention as defined in claim 4, wherein each of said jaw portions comprises a textured gripping surface at the distal end thereof to facilitate tissue manipulation.

9. The invention as defined in claim 1, wherein said jaw portions are configured to define a clearance between the distal end portions thereof when the jaw portions are in said first position in grasping relationship with the anvil shaft to maximize gripping engagement with said anvil shaft.

* * * * *